United States Patent [19]

Nasu et al.

[11] Patent Number: 5,491,239
[45] Date of Patent: Feb. 13, 1996

[54] METHOD FOR HALOGENATING AN AROMATIC COMPOUND

[75] Inventors: Rikuo Nasu; Motohiko Hamaguchi; Hayato Ariyoshi, all of Yokkaichi, Japan

[73] Assignee: Ishihara Sangyo Kaisha Ltd., Osaka, Japan

[21] Appl. No.: 144,525

[22] Filed: Nov. 2, 1993

[30] Foreign Application Priority Data

| Nov. 4, 1992 | [JP] | Japan | 4-336537 |
| Nov. 20, 1992 | [JP] | Japan | 4-352273 |
| Dec. 7, 1992 | [JP] | Japan | 4-358093 |
| Dec. 26, 1992 | [JP] | Japan | 4-362020 |
| Feb. 15, 1993 | [JP] | Japan | 5-065874 |

[51] Int. Cl.⁶ .................. C07D 213/61; C07D 213/73
[52] U.S. Cl. ............... 546/345; 546/286; 546/303; 546/304
[58] Field of Search ................... 546/345, 286, 546/303, 304

[56] References Cited

U.S. PATENT DOCUMENTS 3,901,899  8/1975  Gassman ..................... 546/113

FOREIGN PATENT DOCUMENTS 0476607  3/1992  European Pat. Off. .

OTHER PUBLICATIONS

Thomas E. Nickson, *Synthesis*, pp. 669–670, "A Convenient Procedure for the Chlorination of Deactivated Anilines", 1985.
Patent Abstracts of Japan, vol. 005, No. 168 (C–077), Oct. 27, 1981, JP–A–56097271, Aug. 5, 1981.
Kress, Thomas J., *J. Org. Chem.*, pp. 93–96, vol. 41, No. 1, "Selective Chlorinations in Sulfuric Acid. Synthesis of Some 2–Amino–5–Chloro–,2–Amino–3–Chloro–, and 2–Amino–3,5–Dichloropyridines",1976.
Synthesis, No. 6, Jun. 1990, pp. 499–501, Koch, et al., "Chemistry of 3–Hydroxypyridine Part 2: Synthesis of 5,6–Dihalo–3–Hydroxypyridines".
Chemical Abstracts, vol. 70, 1969, AN 106327x, Tadeusz Batkowski, "3–Halo–5–Nitropyridines", p. 321.
The Chemical Society of Japan, 1992, No. 5, pp. 586–589, "Novel Bromination Methods of 2–Acetamidepyridines".
Aust. J. Chem., 1976, vol. 29, pp. 367–374, Kenneth J. Chapman, et al., "Synthesis and Characterization of N–Chloro–O–Nitroanilines".
J. Org. Chem., vol. 41, No. 19, 1976, pp. 3170–3175, Denis F. Paul, et al., "Chlorination of Anilines. Bimolecular Acid–Catalyzed Rearrangement of N–Chloroanilines".

*Primary Examiner*—C. Warren Ivy
*Assistant Examiner*—D. Margaret M. Mach
*Attorney, Agent, or Firm*—Oblon, Spivak, McClelland, Maier, & Neustadt

[57] ABSTRACT

A method for halogenating an aromatic compound, which comprises reacting the aromatic compound of the formula (I):

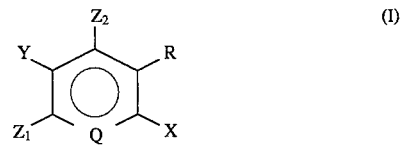

wherein X is a hydroxyl group, an amino group or an acylamino group, each of $Z_1$ and $Z_2$ is a hydrogen atom or a halogen atom, one of R and Y is a hydrogen atom and the other is a nitro group, a cyano group or a trifluoromethyl group, and Q is a nitrogen atom or —C(T)= (wherein T is a hydrogen atom, a halogen atom, a nitro group, a cyano group or a trifluoromethyl group), with a halogenating agent to obtain a 3-halogenoaromatic compound of the formula (II):

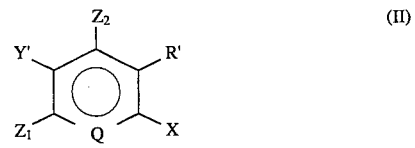

wherein one of R' and Y' is a halogen atom and the other is a nitro group, a cyano group or a trifluoromethyl group, and X, $Z_1$, $Z_2$ and Q are as defined above.

10 Claims, No Drawings

METHOD FOR HALOGENATING AN AROMATIC COMPOUND

The present invention relates to an industrially advantageous method for producing 3-halogenoaromatic compounds, particularly 3-halogenopyridines, which are useful as intermediates for pharmaceuticals or agricultural chemicals. The 3-halogenopyridines are useful, for example, as intermediates for anilinopyridines which are active ingredients of fungicides or insecticides disclosed in e.g. Japanese Unexamined Patent Publications No. 92272/1981 and No. 270266/1992 and German Patent Publication No. 3925238.

Heretofore, it has been known that 3-halogenopyridines such as 2-amino-3-chloro-5-trifluoromethylpyridine can be produced by various methods. For example, Japanese Unexamined Patent Publication No. 97271/1981 discloses at page 654 a method for producing 2-amino-3-chloro-5-trifluoromethylpyridine, which comprises dissolving 2-amino-5-trifluoromethylpyridine in concentrated hydrochloric acid and blowing and reacting chlorine gas thereto. By this method, the desired 2-amino-3-chloro-5-trifluoromethylpyridine can be formed in a small amount. However, this method has a difficulty from the viewpoint of industrial applicability, since many by-products are produced in substantial amounts, and it is difficult to satisfactorily separate the desired product from the reaction products, whereby the yield of the desired product is low.

Accordingly, it has been desired to develop a method whereby by-products will not be formed substantially and the desired product can be obtained satisfactorily in the above-mentioned conventional method for producing a desired 3-halogenopyridine such as 2-amino-3-chloro-5-trifluoromethylpyridine by halogenating a pyridine such as 2-amino-5-trifluoromethylpyridine.

The present inventors have found that when a certain specific halogenating reaction is followed by a rearrangement reaction in the above-mentioned conventional method, the desired reaction efficiently proceeds, whereby the above problem can be solved. The present invention has been accomplished on the basis of this discovery.

Thus, the present invention provides a method for producing a 3-halogenoaromatic compound, which comprises reacting an aromatic compound of the formula (I):

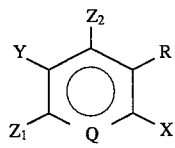

(I)

wherein X is a hydroxyl group, an amino group or an acylamino group, each of $Z_1$ and $Z_2$ is a hydrogen atom or a halogen atom, one of R and Y is a hydrogen atom and the other is a nitro group, a cyano group or a trifluoromethyl group, and Q is a nitrogen atom or —C(T)= (wherein T is a hydrogen atom, a halogen atom, a nitro group, a cyano group or a trifluoromethyl group), with a halogenating agent to obtain a 3-halogenoaromatic compound of the formula (II):

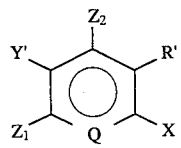

(II)

wherein one of R' and Y' is a halogen atom and the other is a nitro group, a cyano group or a trifluoromethyl group, and X, $Z_1$, $Z_2$ and Q are as defined above, wherein the aromatic compound of the formula (I) is reacted with a halogenating agent to form a halogenoaromatic compound of the formula (III):

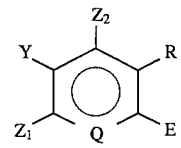

(III)

wherein E is —O—Hal or

—N-Hal
|
A (wherein A is a hydrogen atom or an acyl group, and Hal is a halogen atom), and $Z_1$, $Z_2$, R, Y and Q are as defined above, and this halogenoaromatic compound of the formula (III) is subjected to a rearrangement reaction in the presence of a proton donor to form the 3-halogenoaromatic compound of the formula (II).

Further, the present invention provides a method for producing a 3-halogenopyridine, which comprises reacting a pyridine of the formula (I'):

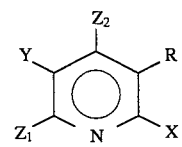

(I')

wherein X is a hydroxyl group, an amino group or an acylamino group, each of $Z_1$ and $Z_2$ is a hydrogen atom or a halogen atom, and one of R and Y is a hydrogen atom and the other is a nitro group, a cyano group or a trifluoromethyl group, with a halogenating agent to obtain a 3-halogenopyridine of the formula (II'):

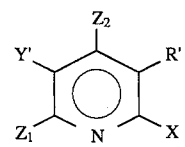

(II')

wherein one of R' and Y' is a halogen atom and the other is a nitro group, a cyano group or a trifluoromethyl group, and X, $Z_1$ and $Z_2$ are as defined above, wherein the pyridine of the formula (I') is reacted with a halogenating agent to form a halogenopyridine of the formula (III'):

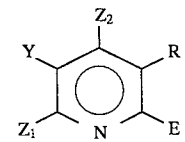

(III')

wherein E is —O—Hal or

—N-Hal
|
A (wherein A is a hydrogen atom or an acyl group, and Hal is a halogen atom), and $Z_1$, $Z_2$, R and Y are as defined above, and this halogenopyridine of the formula (III') is subjected to a rearrangement reaction in the presence of a proton donor to form the 3-halogenopyridine of the formula (II').

Still further, the present invention provides a method for producing a 3-halogenopyridine, which comprises subjecting a halogenopyridine of the formula (III'):

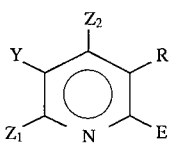

(III')

wherein E is —O—Hal or

(wherein A is a hydrogen atom or an acyl group, and Hal is a halogen atom), each of $Z_1$ and $Z_2$ is a hydrogen atom or a halogen atom, and one of R and Y is a hydrogen atom and the other is a nitro group, a cyano group or a trifluoromethyl group, to a rearrangement reaction in the presence of a proton donor to obtain a 3-halogenopyridine of the formula (II'):

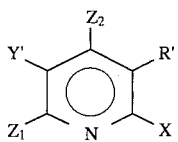

(II')

wherein one of R' and Y' is a halogen atom and the other is a nitro group, a cyano group or a trifluoromethyl group, X is a hydroxyl group, an amino group or an acylamino group, and $Z_1$ and $Z_2$ are as defined above.

Furthermore, the present invention provides a halogenopyridine derivative of the formula (V):

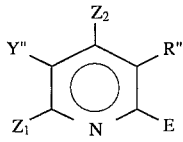

(V)

wherein E is —O—Hal or

(wherein A is a hydrogen atom or an acyl group, and Hal is a halogen atom), each of $Z_1$ and $Z_2$ is a hydrogen atom or a halogen atom, one of R" and Y" is a hydrogen atom or a halogen atom and the other is a nitro group, a cyano group or a trifluoromethyl group.

Now, the present invention will be described in detail with reference to the preferred embodiments.

In the formulas (I) to (III), (I') to (III'), (V) and (IV) which will be given hereinafter, the halogen atom for $Z_1$ and $Z_2$ may, for example, be fluorine, chlorine or bromine, preferably chlorine; the acylamino group for X may, for example, be an alkylcarbonylamino group, preferably an acetylamino group; and the halogen atom for R', Y', R", Y" and Hal may, for example, be chlorine or bromine, preferably chlorine.

The aromatic compound of the formula (I) includes, for example, 2-chloro-6-nitroaniline, and 2-chloro-6-nitrophenol in addition to pyridines given below, but the pyridines are preferred. The pyridines represented by the formula (I) include, for example, 2-amino-5-nitropyridine, 2-amino-5-cyanopyridine, amino trifluoromethylpyridines such as 2-amino-5-trifluoromethylpyridine, 2-amino-6-chloro-5-trifluoromethylpyridine, 2-amino-3-trifluoromethylpyridine and 2-amino-6-chloro-3-trifluoromethylpyridine, and hydroxy trifluoromethylpyridines such as 2-hydroxy-5-trifluoromethylpyridine and 2-hydroxy-3-trifluoromethylpyridine, but amino trifluoromethylpyridines are particularly preferred among them.

The 3-halogenoaromatic compound of the formula (II) includes, for example, 2,4-dichloro-6-nitroaniline and 2,4-dichloro-6-nitrophenol in addition to 3-halogenopyridines given below, but the 3-halogenopyridines are preferred. The 3-halogenopyridines represented by the formula (II) include, for example, 2-amino-3-chloro-5-nitropyridine, 2-amino-3-chloro-5-cyanopyridine, 3-halogeno amino trifluoromethylpyridines such as 2-amino-3-chloro-5-trifluoromethylpyridine, 2-amino-3,6-dichloro-5-trifluoromethylpyridine and 2-amino-5-chloro-3-trifluoromethylpyridine, and 3-halogeno hydroxy trifluoromethylpyridines such as 2-hydroxy-3-chloro-5-trifluoromethylpyridine and 2-hydroxy-5-chloro-3-trifluoromethylpyridine, but 3-halogeno amino trifluoromethylpyridines are particularly preferred among them.

The halogenoaromatic compound of the formula (III) includes, for example, 2-chloroamino-3-chloronitrobenzene and 2-chloroxy-3-chloronitrobenzene in addition to halogenopyridines given below, but the halogenopyridines are preferred. The halogenopyridine or the halogenopyridine derivative of the formula (III') or (V) includes, for example, 2-chloroamino-5-nitropyridine, 2-chloroamino-5-cyanopyridine, 2-halogenoamino trifluoromethylpyridines such as 2-chloroamino-5-trifluoromethylpyridine, 2-chloroamino-6-chloro-5-trifluoromethylpyridine and 2-chloroamino-3-trifluoromethylpyridine, 2-chloroamino-3-chloro-5-nitropyridine, 2-chloroamino-3-chloro-5-cyanopyridine, 2-halogenoamino-3-halogeno trifluoromethylpyridines such as 2-chloroamino-3-chloro-5-trifluoromethylpyridine and 2-chloroamino-3,6-dichloro-5-trifluoromethylpyridine, 2-halogenoxy trifluoromethylpyridines such as 2-chloroxy-5-trifluorome thylpyridine and 2-chloroxy-3-trifluorome thylpyridine, and 2-halogenoxy-3-halogeno trifluorome thylpyridines such as 2-chloroxy-3-chloro-5-trifluorome thylpyridine, but 2-halogenoamino trifluorome thylpyridines and 2-halogenoamino-3-halogeno trifluorome thylpyridines are particularly preferred among them.

The pyridine of the formula (I') may be the one produced by various methods. However, in the case of the above-mentioned amino trifluoromethylpyridines, it is preferred to use a copper catalyst such as cuprous chloride or cupric chloride or a phase transfer catalyst such as quaternary ammonium salt or a quaternary phosphonium salt, as a reaction catalyst, in the amination of halogeno trifluoromethylpyridines with ammonia, whereby the reaction treatment can be sufficiently carried out. The above catalyst is used usually in an amount of from about 0.005 to 0.1 mol, preferably from about 0.01 to 0.05 mol, per mol of the halogeno trifluoromethylpyridines.

In the method of the present invention, the desired reaction can be conducted by mixing and stirring the aromatic compound of the formula (I) and the halogenating agent. The halogenating agent may be of any type so long as it is capable of reacting with the aromatic compound to form the halogenoaromatic compound of the formula (III). When an N-halogenosuccinimide or an N-halogenophthalimide is used as the halogenating agent, N-chlorosuccinimide, N-bromosuccinimide, N-chlorophthalimide or N-bromophthalimide may, for example, be employed, but N-chlorosuccinimide or N-chlorophthalimide is preferred. As the halogenating agent, a tert-butyl hypohalide such as tert-butyl hypochloride, chlorine gas or bromine may also be used. Further, as the halogenating agent, a trihalogenoisocyanuric acid or a salt thereof, or a dihalogenoisocyanuric acid or a salt thereof, may be employed. For example, trichloroisocyanuric acid, tribromoisocyanuric acid, dichloroisocyanuric acid or dibromoisocyanuric acid, or a sodium or potassium salt thereof may, for example, be employed, but trichloroisocyanuric acid or dichloroisocyanuric acid, or a salt thereof is preferred. Furthermore, as a halogenating agent, a halogeno 3-halogenoaromatic compound having X at the 2-position of the 3-halogenoaromatic compound of the formula (II) halogenated, may be used, but it is preferred to use a halogeno 3-halogenopyridine of the formula (IV):

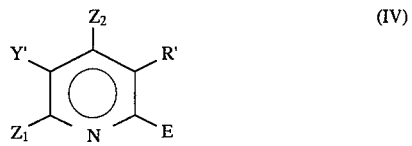
(IV)

wherein R', Y', E, $Z_1$ and $Z_2$ are as defined above, particularly 2-chloroamino-3-chloro-5-nitropyridine, 2-chloroamino-3-chloro-5-cyanopyridine or 2-chloroamino-3-chloro-5-trifluoromethylpyridine. Such a halogenating agent is suitably selected depending upon the desired 3-halogenoaromatic compound. However, from the industrial point of view, N-chlorosuccinimide, trichloroisocyanuric acid, a salt of dichloroisocyanuric acid, chlorine gas, bromine or chloro 3-chloropyridine among the compounds of the formula (IV), is preferred, and chlorine gas, bromine or chloro 3-chloropyridine is particularly preferred.

In the method of the present invention, the reaction is usually conducted by dissolving, suspending or dispersing the starting material in the presence of a solvent inert to this halogenating reaction. Such a solvent may, for example, be water; a halogenated aliphatic hydrocarbon such as carbon tetrachloride, methylene chloride or 1,2-dichloroethane; a monocyclic or alicyclic aromatic hydrocarbon such as benzene, chlorobenzene, toluene or cyclohexane; a nitrile such as acetonitrile or propionitrile; an alcohol such as methanol or ethanol; an ester such as ethyl acetate or propyl acetate; or a ketone such as acetone or methyl isobutyl ketone. These solvents may be used alone or in combination as a mixture of two or more.

In the method of the present invention, the reaction rate of the desired halogenation reaction can be increased by the presence of an azobisnitrile type compound such as 2,2'-azobisisobutyronitrile, 2-azobis-2-methylbutyronitrile, 2,2'-azobisisopropionitrile or 4,4'-azobis-4-cyanovaleric acid, or a benzoyl peroxide type compound such as benzoyl peroxide or 3,3'-dimethylbenzoyl peroxide, as a catalyst.

The amounts of the aromatic compound of the formula (I) as the starting material, the N-halogenosuccinimide, the N-halogenophthalimide, the tert-butyl hypohalide or the halogeno 3-halogenoaromatic compound as the halogenating agent, the solvent and the catalyst used in the method of the present invention, can not be generally defined, since they vary depending upon the differences of the types of these materials, the reaction conditions, etc. However, the N-halogenosuccinimide, the N-halogenophthalimide, the tert-butyl hypohalide or the halogeno 3-halogenoaromatic compound is usually from 1.0 to 1.5 mols, the solvent is from 0.5 to 20 parts by weight, and the catalyst is from 0.001 to 0.02 mmol, per mol of the aromatic compound of the formula (I) as the starting material. In such a case, the reaction temperature and the reaction time likewise vary depending upon the differences of the types of the starting material and the halogenating agent, the presence or absence, or the type of the solvent or the catalyst. However, the reaction is usually completed at a temperature of from −20° C. to the refluxing temperature of the solvent within from 0.5 to 24 hours.

Further, when a trihalogenoisocyanuric acid or a salt thereof, or a dihalogenoisocyanuric acid or a salt thereof, is used as the halogenating agent in the method of the present invention, the amount of such a substance likewise can not generally be defined since it varies depending upon the differences of the type of the halogenating agent, the reaction conditions, etc. However, the trihalogenoisocyanuric acid or its salt is used usually in an amount of from 0.3 to 1.0 mol and the dihalogenoisocyanuric acid or its salt is used usually in an amount of from 0.5 to 1.5 mol, per mol of the aromatic compound of the formula (I). In such a case, the reaction temperature and the reaction time vary depending upon the differences of various reaction conditions, but the reaction is usually completed at a temperature of from −20° C. to the refluxing temperature of the solvent within from 0.5 to 24 hours.

Further, when chlorine gas or bromine is used as the halogenating agent in the method of the present invention, the amount likewise can not generally be defined, but the chlorine gas or bromine is used usually in an amount of from 0.5 to 1.0 mol per mol of the aromatic compound of the formula (I). In such a case, the reaction temperature and the reaction time likewise can not generally be defined, but the reaction is usually completed at a temperature of from −20° C. to the refluxing temperature of the solvent, preferably from 0° C. to the refluxing temperature of the solvent, within from 0.5 to 24 hours. Further, the conditions for chlorinating 2-amino-5-trifluoromethylpyridine with chlorine gas likewise can not generally be defined, but the reaction is usually conducted at a temperature of from −20° C. to 20° C. Thus, according to the method of the present invention, the halogenoaromatic compound of the formula (III) can satisfactorily be formed.

The halogeno 3-halogenopyridine of the formula (IV) can be produced substantially in the same manner as the method for halogenating the above pyridine.

Then, in the method of the present invention, a rearrangement reaction is conducted to rearrange the halogenoaromatic compound of the formula (III) in the presence of a proton donor. The reaction temperature and the reaction time for this rearrangement reaction likewise vary depending upon differences of the type of the starting material, the proton donor, the presence or absence, or the type of a solvent or a catalyst. However, the reaction is usually completed at a temperature of from 0° C. to the refluxing temperature of the solvent, preferably from 20° C. to the refluxing temperature of the solvent, within from 0.5 to 24 hours, whereby the desired 3-halogenoaromatic compound of the formula (II) can satisfactorily be formed. The proton donor may, for example, be a carboxylic acid such as formic acid, acetic acid, propionic acid, oxalic acid, succinic acid or benzoic acid, succinimide, phthalimide, or isocyanuric acid, but preferred is at least one carboxylic acid selected from the group consisting of formic acid, acetic acid and propionic acid.

When an N-halogenosuccinimide, an N-halogenophthalimide, a trihalogenoisocyanuric acid or its salt, or a dihalogenoisocyanuric acid or its salt, is used as the halogenating agent, succinimide, phthalimide or isocyanuric acid will be formed as a by-product and will serve as a proton donor, whereby it is unnecessary to separately add a proton donor, or to conduct the halogenating reaction and the rearrangement reaction separately. However, when chlorine gas, bromine, a tert-butyl hypohalide or the above-mentioned halogeno 3-halogenoaromatic compound is used as the halogenating agent, a proton donor is added usually in an amount of at least 0.01 mol, preferably from 0.01 to 0.2 mol, per mol of the halogenoaromatic compound of the formula (III). In such a case, the rearrangement reaction will be completed usually at a temperature of from 0° C. to the refluxing temperature of the solvent within from 0.5 to 24 hours.

After completion of the reaction, the reaction product is subjected to usual purification or separation to separate the desired product. However, when the aromatic compound of the formula (I) is halogenated with an N-halogenosuccinimide, an N-halogenophthalimide, a trihalogenoisocyanuric acid or its salt, or a dihalogenoisocyanuric acid or its salt, the reaction product may usually be cooled, and then succinimide, phthalimide or isocyanuric acid formed as a by-product by the reaction, may be recovered by filtration, while an acidic aqueous solution is added to the oil layer to form a salt of the desired product, and the aqueous layer may be neutralized to separate the desired product. Thus, the desired product can be obtained, for example, in a yield of at least 70%.

Further, with respect to the recovered succinimide, phthalimide or isocyanuric acid, after cooling the reaction product, an aqueous alkaline solution of e.g. sodium hydroxide or potassium hydroxide, is added thereto to separate an aqueous layer and an oil layer, whereupon chlorine gas is blown into the aqueous layer, or bromine is dropwise added to the aqueous layer, to form N-chlorosuccinimide, N-bromosuccinimide, N-chlorophthalimide, trichloroisocyanuric acid or its salt, or dichloroisocyanuric acid or its salt, which may be recycled for reuse.

Further, when the aromatic compound of the formula (I) is halogenated with chlorine gas or bromine, a hydrohalogenate of the aromatic compound will be formed as a by-product, this hydrohalogate may be treated with an alkaline substance to obtain the aromatic compound, which may be recycled for reuse as a starting material, as follows.

The 3-halogenoaromatic compound produced by the above-mentioned method, is halogenated in the same manner as in the halogenation reaction of the aromatic compound of the formula (I), to form a halogeno 3-halogenoaromatic compound, and then the aromatic compound of the formula (I) is halogenated with this halogeno 3-halogenoaromatic compound to form a halogenoaromatic compound of the formula (III), whereupon this halogenoaromatic compound is subjected to the rearrangement reaction to obtain a 3-halogenoaromatic compound. By combining such a method for producing the 3-halogenoaromatic compound and a method for treating with a suitable alkaline substance, the hydrohalogenate of a 3-halogenoaromatic compound produced as a by-product when the 3-halogenoaromatic compound is halogenated with chlorine gas or bromine, it is theoretically possible to produce three times by equivalent of the 3-halogenoaromatic compound from two times by equivalent of the 3-halogenoaromatic compound and one equivalent of the aromatic compound. The desired 3-halogenoaromatic compound can be produced industrially advantageously by conducting the halogenation reaction and the rearrangement reaction sequentially while recycling a part of the three times by equivalent of the 3-halogenoaromatic compound thus obtained.

Now, the present invention will be described in further detail with reference to Examples. However, it should be understood that the present invention is by no means restricted by such specific Examples.

EXAMPLE 1

(1) Into an autoclave made of SUS-316 and having an internal capacity of 2 l, 363 g (2.0 mols) of 2-chloro-5-trifluoromethylpyridine, 19.8 g (0.2 mol) of cuprous chloride and 1,275 g (30.0 mols as $NH_3$) of 40% aqueous ammonia were added, and the reaction was carried out at 120° C. for 16 hours under heating with stirring. After completion of the reaction, the reaction mixture was cooled to room temperature and separated into an aqueous ammonia layer and an oil layer, whereby 335 g of an oil containing 1.5% of the starting material 2-chloro-5-trifluoromethylpyridine and 91% of 2-amino-5-trifluoromethylpyridine (as analyzed by liquid chromatography) was obtained.

This oil was further distilled under reduced pressure to obtain 278 g of 2-amino-5-trifluoromethylpyridine (melting point: 42.5° C., purity as measured by liquid chromatography: 99%, yield: 85%).

(2) Into a 300 ml four-necked flask equipped with a stirrer, a thermometer and a reflux condenser, 16.2 g (0.1 mol) of 2-amino-5-trifluoromethylpyridine prepared in the above step, 16.7 g (0.125 mol) of N-chlorosuccinimide and 150 g of acetonitrile were added, and the reaction was conducted at 50° C. for 5 hours under heating with stirring. During the reaction, formation of 2-chloroamino-5-trifluoromethylpyridine was confirmed. After completion of the reaction, acetonitrile was distilled off, and to the remaining reaction product, 100 g of a 10% sodium hydroxide aqueous solution and 100 g of methylene chloride were added and stirred. An aqueous layer and a methylene chloride layer were separated, and the methylene chloride layer was concentrated to obtain 20.2 g of yellow crystals containing 85% of 2-amino-3-chloro-5-trifluoromethylpyridine and 2% of the starting material 2-amino-5-trifluoromethylpyridine (yield of 2-amino-3-chloro-5-trifluoromethylpyridine: 87.4%).

EXAMPLE 2

(1) The reaction and the post treatment were conducted in the same manner as in step (1) of Example 1 except that 32.2 g (0.1 mol) of tetra-n-butylammonium bromide was used instead of 19.8 g (0.2 mol) of cuprous chloride in step (1) of Example 1, to obtain 284 g of 2-amino-5-trifluoromethylpyridine (purity as measured by liquid chromatography: 99%, yield: 87%).

(2) Into the same 300 ml four-necked flask as used in Example 1, 16.2 g (0.1 mol) of 2-amino-5-trifluoromethylpyridine prepared in the above step, 16.7 g (0.125 mol) of N-chlorosuccinimide and 150 g of methylene chloride were added, and the reaction was carried out at 40° C. for 24 hours under heating with stirring. During the reaction, formation of 2-chloroamino-5-trifluoromethylpyridine was confirmed. After completion of the reaction, methylene chloride was distilled off. To separate succinimide and the desired product, 150 g of diethyl ether was put into the remaining reaction product, and the mixture was stirred. Precipitated succinimide was separated by filtration, and the diethyl ether solution was concentrated to obtain 18.2 g of yellow crystals containing 89% of 2-amino-3-chloro-5-trifluoromethylpyridine and 0.3% of the starting material 2-amino-5-trifluoromethylpyridine (yield of 2-amino-3-chloro-5-trifluoromethylpyridine: 82.4%).

The succinimide obtained by filtration was 11.5 g after drying (purity as measured by gas chromatography: 98%, recovery rate: 93%).

EXAMPLE 3

(1) The reaction and the post treatment were conducted in the same manner as in step (1) of Example 1 except that 33.9 g (0.1 mol) of tetra-n-butylphosphonium bromide was used instead of 19.8 g (0.2 mol) of cuprous chloride in step (1) of Example 1, to obtain 288 g of 2-amino-5-trifluoromethylpyridine (purity as measured by liquid chromatography: 99%, yield: 88%).

(2) Into the same 300 ml four-necked flask as used in Example 1, 16.2 g (0.1 mol) of 2-amino-5-trifluoromethylpyridine prepared in the above step, 16.7 g (0.125 mol) of N-chlorosuccinimide and 150 g of 1,2-dichloroethane were added, and the reaction was carried out at 80° C. for one hour under heating with stirring. During the reaction, formation of 2-chloroamino-5-trifluoromethylpyridine was confirmed. After completion of the reaction, the reaction mixture was cooled to room temperature, and 100 g of water was added thereto and stirred. An aqueous layer and an oil layer were separated. Water in the aqueous layer was distilled off under reduced pressure to obtain 10.4 g of white crystals of succinimide (purity as measured by gas chromatography: 98.8%, recovery rate: 84%).

On the other hand, a 20% hydrochloric acid aqueous solution was added to the oil layer obtained by liquid separation, and the mixture was stirred. An aqueous layer and an oil layer were separated, and the aqueous layer was neutralized with a 25% sodium hydroxide aqueous solution. Precipitated slightly yellow crystals were collected by filtration and dried to obtain 15.4 g of 2-amino-3-chloro-5-trifluoromethylpyridine (purity as measured by liquid chromatography: 96%, yield: 75%).

EXAMPLE 4

The reaction and the post treatment were conducted in the same manner as in Example 3 except that 150 g of benzene was used instead of 150 g of 1,2-dichloroethane as the solvent, and 0.1 g of 2,2'-azobisisobutyronitrile was added in Example 3. The amount of succinimide obtained was 10.9 g (purity as measured by gas chromatography: 98.7%, recovery rate: 88%), and the amount of 2-amino-3-chloro-5-trifluoromethylpyridine obtained was 15.9 g (purity as measured by liquid chromatography: 96%, yield: 78%).

EXAMPLE 5

The reaction and the post treatment were conducted in the same manner as in Example 3 except that 150 g of toluene was used instead of 150 g of 1,2-dichloroethane as the solvent in Example 3. The amount of succinimide obtained was 11.0 g (purity as measured by gas chromatography: 98.7%, recovery rate: 88%), and the amount of 2-amino-3-chloro-5-trifluoromethylpyridine obtained was 16.0 g (purity as measured by liquid chromatography: 97%, yield: 79%).

EXAMPLE 6

Into a 300 ml four-necked flask equipped with a stirrer, a thermometer and a reflux condenser, 16.2 g (0.1 mol) of 2-amino-5-trifluoromethylpyridine prepared in the same manner as in step (1) of Example 1, 8.8 g (0.038 mol) of trichloroisocyanuric acid and 150 g of acetonitrile were added, and the reaction was carried out at 60° C. for one hour under heating. During the reaction, formation of 2-chloroamino-5-trifluoromethylpyridine was confirmed. After completion of the reaction, the reaction mixture was cooled, and precipitated isocyanuric acid was separated by filtration. The acetonitrile solution was concentrated to obtain 19.9 g of yellow crystals containing 92.1% of 2-amino-3-chloro-5-trifluoromethylpyridine and 0.6% of the starting material 2-amino-5-trifluoromethylpyridine (yield of 2-amino-3-chloro-5-trifluoromethylpyridine: 93.3%).

Further, to this yellow crystals, 100 g of a 20% hydrochloric acid aqueous solution and 75 g of toluene were added and stirred. An aqueous layer and an oil layer were separated, and the aqueous layer was neutralized with a 25% sodium hydroxide aqueous solution. Precipitated slightly yellow crystals were collected by filtration and dried to obtain 15.9 g of 2-amino-3-chloro-5-trifluoromethylpyridine (purity as measured by liquid chromatography: 96%, yield: 77.7%).

Further, the isocyanuric acid obtained by filtration was 4.7 g after drying (recovery rate: 96%).

EXAMPLE 7

Into the same 300 ml four-necked flask as used in Example 1, 16.2 g (0.1 mol) of 2-amino-5-trifluoromethylpyridine prepared in the same manner as in step (1) of Example 1, 10.1 g (0.043 mol) of trichloroisocyanuric acid and 150 g of toluene were added, and the reaction was conducted at 110° C. for 3 hours under heating with stirring. During the reaction, formation of 2-chloroamino-5-trifluoromethylpyridine was confirmed. After completion of the reaction, the reaction mixture was cooled to room temperature, and 100 g of a 25% sodium hydroxide aqueous solution was added thereto and stirred. An aqueous layer and an oil layer were separated. A 20% hydrochloric acid aqueous solution was added to the oil layer, and the mixture was stirred. An aqueous layer and an oil layer were further separated. The aqueous layer was neutralized with a 25% sodium hydroxide aqueous solution. Precipitated slightly yellow crystals were collected by filtration and dried to obtain 17.6 g 2-amino-3-chloro-5-trifluoromethylpyridine (purity as measured by liquid chromatography: 95%, yield: 85%).

EXAMPLE 8

Into the same 300 ml four-necked flask as used in Example 1, 16.2 g (0.1 mol) of 2-amino-5-trifluoromethylpyridine and 150 g of toluene were added, and 42.2 g of a 30% sodium dichloroisocyanurate aqueous solution (sodium dichloroisocyanurate: 0.0575 mol) was dropwise added thereto over a period of one hour while stirring at 20° C. After the dropwise addition, the reaction mixture was heated to 80° C., and the reaction was conducted for 10 hours with stirring. During the reaction, formation of 2-chloroamino-5-trifluoromethylpyridine was confirmed. After completion of the reaction, the reaction mixture was cooled to room temperature, and an aqueous layer and an oil layer were separated. A 20% hydrochloric acid aqueous solution was added to the oil layer, and the mixture was stirred. An aqueous layer and an oil layer were further separated. The aqueous layer was neutralized with a 25% sodium hydroxide aqueous solution. Precipitated slightly yellow crystals were collected by filtration and dried to obtain 15.7 g 2-amino-3-chloro-5-trifluoromethylpyridine (purity as measured by liquid chromatography: 96%, yield: 77%).

EXAMPLE 9

Into the same 300 ml four-necked flask as used in Example 1, 16.2 g (0.1 mol) of 2-amino-5-trifluoromethylpyridine, 20.9 g (0.115 mol) of N-chlorophthalimide and 150 g of toluene were added, and the reaction was carried out at 80° C. for one hour under heating with stirring. During the reaction, formation of 2-chloroamino-5-trifluoromethylpyridine was confirmed. After completion of the reaction, the reaction mixture was cooled to room temperature, and 50 g of a 25% sodium hydroxide aqueous solution was added thereto and stirred. An aqueous layer and an oil layer were separated. A 20% hydrochloric acid aqueous solution was added to the oil layer, and the mixture was stirred. An aqueous layer and an oil layer were separated again. The aqueous layer was neutralized with a 25% sodium hydroxide aqueous solution. Precipitated slightly yellow crystals were collected by filtration and dried to obtain 17.5 g 2-amino-3-chloro-5-trifluoromethylpyridine (purity as measured by liquid chromatography: 97%, yield: 86%).

EXAMPLE 10

Into the same 300 ml four-necked flask as used in Example 1, 16.2 g <0.1 mol) of 2-amino-5-trifluoromethylpyridine and 150 g of toluene were added, and 10.1 g (0.043 mol) of trichloroisocyanuric acid was added in a divided fashion over a period of one hour while stirring and cooling to a temperature of from 0° to 5° C. After the addition, the reaction was carried out at the same temperature for 3 hours with stirring. The reaction mixture was analyzed by liquid chromatography, whereby 2-chloroamino-5-trifluoromethylpyridine was 91%, and 2-amino-3-chloro-5-trifluormethylpyridine was 6%. Then, the reaction mixture was heated to 80° C., and the rearrangement reaction was conducted for two hours with stirring. The reaction product was analyzed by liquid chromatography, whereby the peak of 2-chloroamino-5-trifluoromethylpyridine was found to have disappeared, and 2-amino-3-chloro-5-trifluoromethylpyridine was 90%. After completion of the reaction, the reaction mixture was cooled, and the post treatment was carried out in the same manner as in Example 9 to obtain 16.0 g of 2-amino- 3-chloro-5-trifluoromethylpyridine (purity as measured by liquid chromatography: 97%, yield: 79%).

EXAMPLE 11

Into the same 300 ml four-necked flask as used in Example 1, 13.9 g (0.1 mol) of 2-amino-5-nitropyridine, 15.4 g (0.115 mol) of N-chlorosuccinimide and 150 g of toluene were added, and the reaction was carried out at 80° C. for one hour under heating with stirring. During the reaction, formation of 2-chloroamino-5-nitropyridine was confirmed. After completion of the reaction, the reaction mixture was cooled to room temperature, and 100 g of water was added thereto and stirred. An aqueous layer and an oil layer were separated. Toluene in the oil layer was distilled off under reduced pressure to obtain 18.0 g of yellow crystals containing 91% of 2 -amino-3-chloro-5-nitropyridine and 0.7% of the starting material 2-amino-5-nitropyridine (yield of 2-amino-3 -chloro-5-nitropyridine: 94.4%).

EXAMPLE 12

Into a 300 ml four-necked flask equipped with a stirrer, a thermometer, a dropping funnel and a reflux condenser, 16.2 g (0.1 mol) of 2-amino-5-trifluoromethylpyridine prepared in the same manner as in step (1) of Example 1 and 75 g of toluene were added, and the mixture was cooled to a temperature of from 0° to 5° C., then, a mixed solution comprising 12.5 g (0.115 mol) of tert-butyl hypochloride and 75 g of toluene, was dropwise added thereto from the dropping funnel at the same temperature over a period of one hour. After the dropwise addition, the reaction was conducted at the same temperature for 30 minutes with stirring. The reaction product was analyzed by liquid chromatography, whereby 2 -chloroamino-5-trifluoromethylpyridine was 95%, and 2 -amino-3-chloro-5-trifluoromethylpyridine was 1%.

Then, 0.3 g of acetic acid was added to the reaction product, and the mixture was heated to 70° C., and the rearrangement reaction was conducted for one hour with stirring. The reaction product was analyzed by liquid chromatography, whereby the peak of 2-chloroamino-5-trifluoromethylpyridine was found to have disappeared, and 2-amino-3-chloro-5-trifluoromethylpyridine was 89%. After completion of the reaction, the reaction mixture was cooled to room temperature, and a 20% hydrochloric acid aqueous solution was added and stirred.

An aqueous layer and an oil layer were separated. The aqueous layer was neutralized with a 25% sodium hydroxide aqueous solution. Precipitated slightly yellow crystals were collected by filtration and dried to obtain 17.3 g of 2-amino-3-chloro-5-trifluoromethylpyridine (purity as measured by liquid chromatography: 98%, yield: 86%).

EXAMPLE 13

Into a 300 ml four-necked flask equipped with a stirrer, a thermometer, a gas supply tube and a reflux condenser, 32.4 g (0.2 mol) of 2-amino-5-trifluoromethylpyridine prepared in the same manner as in step (1) of Example 1 and 150 g of toluene were added, and the mixture was cooled to a temperature of from 0° to 5° C. Then, 7.1 g (0.1 mol) of chlorine gas was blown thereinto over a period of 30 minutes with stirring. As soon as the blowing was started, the hydrochloride of 2 -amino-5-trifluoromethylpyridine started to precipitate. The reaction product was analyzed by liquid chromatography, whereby 2-chloroamino-5-trifluoromethylpyridine was 48%, and the hydrochloride of 2-amino-5-trifluoromethylpyridine was 49%.

Then, 1 g of acetic acid was added to the reaction product, and the mixture was heated to 80° C., and the rearrangement reaction was conducted for 30 minutes with stirring. The reaction product was analyzed by liquid chromatography, whereby the peak of 2-chloroamino-5-trifluoromethylpyridine was found to have disappeared, and 2-amino-3-chloro-5-trifluoromethylpyridine was 45%, and the hydrochloride of 2-amino-5trifluoromethylpyridine was 48%. After completion of the reaction, the reaction mixture was cooled, and the hydrochloride of 2-amino-5-trifluoromethylpyridine formed by the reaction and the precipitated, was collected by filtration. A 20% hydrochloric acid aqueous solution was added to the oil layer, and the mixture was stirred. An aqueous layer and an oil layer were further separated. The aqueous layer was neutralized with a 25% sodium hydroxide aqueous solution. Precipitated slightly yellow crystals were collected by filtration and dried to obtain 16.7 g of 2-amino-3-chloro-5-trifluoromethylpyridine (purity as measured by liquid chromatography: 97%, yield: 41.2%).

The hydrochloride of 2-amino-5-trifluoromethylpyridine previously obtained by filtration, was 18.9 g (yield: 47.6%) as dried. This hydrochloride may be dissolved in water, neutralized and then extracted with toluene, so that it can be recycled for reuse as the starting material for the next reaction. The yield of the oil in this reaction is 88.8% in total including 47.6% of the hydrochloride of 2-amino-5-trifluoromethylpyridine and 41.2% of 2-amino-3-chloro-5-trifluoromethylpyridine.

EXAMPLE 14

Into a 300 ml four-necked flask equipped with a stirrer, a thermometer, a gas supply tube and a reflux condenser, 39.3 g, (0.2 mol) of 2-amino-3-chloro-5-trifluoromethylpyridine and 150 g of toluene were added, and the mixture was cooled to a temperature of from 0° to 5° C. Then, 7.1 g (0.1 mol) of chlorine gas was blown thereinto over a period of 30 minutes with stirring. As soon as the blowing was started, the hydrochloride of 2-amino-3-chloro-5-trifluoromethylpyridine started to precipitate. The reaction product was analyzed by liquid chromatography, whereby 2-chloroamino-3-chloro-5-trifluoromethylpyridine was 49%, and the hydrochloride of 2-amino-3-chloro-5-trifluoromethylpyridine was 49%.

Then, 16.2 g (0.1 mol) of 2-amino-5-trifluoromethylpyridine was added to the reaction product, and the mixture was heated to 20° C. and stirred at the same temperature for two hours. The reaction product was analyzed by liquid chromatography, whereby 2-chloroamino-3-chloro-5-trifluoromethylpyridine was found to have decreased to 1%, and 2-chloroamino-5-trifluoromethylpyridine was formed afresh in an amount of 31%, and 2-amino-3-chloro-5-trifluoromethylpyridine was formed in an amount of 30%. The rest was the hydrochloride of 2-amino-3-chloro-5-trimethylpyridine.

Further, 1 g of acetic acid was added to the reaction product, and the mixture was heated to 80° C., and the rearrangement reaction was conducted for 30 minutes with stirring. The reaction product was analyzed by liquid chromatography, whereby the peak of 2-chloroamino-5-trifluoromethylpyridine was found to have disappeared, and 2-amino-3-chloro-5-trifluoromethylpyridine was 63%, and the hydrochloride of 2-amino-3-chloro-5-trifluoromethylpyridine was 32%. After completion of the reaction, the reaction mixture was cooled, and a 20% hydrochloric acid aqueous solution was added to the reaction product and stirred. An aqueous layer and an oil layer were further separated. The aqueous layer was neutralized with a 25% sodium hydroxide aqueous solution. Precipitated slightly yellow crystals were collected by filtration and dried to obtain 55.9 g of 2-amino-3-chloro-5-trifluoromethylpyridine (purity as measured by liquid chromatography: 98%, yield: 92.9%).

EXAMPLE 15

Into a 500 ml four-necked flask equipped with a stirrer, a thermometer and a reflux condenser, 6.0 g (0.05 mol) of 2-amino-5-cyanopyridine, 8.3 g (0.0625 mol) of N-chlorosuccinimide and 200 g of acetonitrile were added, and the reaction was conducted at 50° C. for one hour with stirring. During the reaction, the reaction product was analyzed by liquid chromatography, whereby formation of 2-chloroamino-5-cyanopyridine was confirmed. After completion of the reaction, acetonitrile was distilled off. To separate succinimide and the desired product, 50 g of water was added to the remaining product, and the mixture was stirred. Precipitated crystals were collected by filtration, washed with 50 g of toluene and dried to obtain 6.9 g of 2-amino-3-chloro-5-cyanopyridine as slightly brown crystals (purity as measured by liquid chromatography: 98%, yield: 88%).

The melting point of this product was 193.9° to 194.0° C. (not corrected), and the result of the mass spectrometry was $M^+$: 153, $M^+$—Cl: 118.

According to the present invention, the 3-halogenoaromatic compound of the formula (II) can be formed from the aromatic compound of the formula (I) by a simple process and operation for the reaction without accompanying any substantial side reactions. Thus, the method of the present invention is industrially useful.

We claim:
1. A method for halogenating pyridine, which comprises reacting a pyridine of the formula (I'):

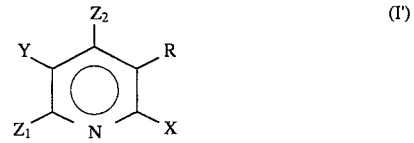

wherein X is amino; each of $Z_1$ and $Z_2$ is hydrogen or halogen; one of R and Y is hydrogen and the other is nitro, cyano or trifluoromethyl; with a halogenating agent to form a 3-halogenopyridine of the formula (II'):

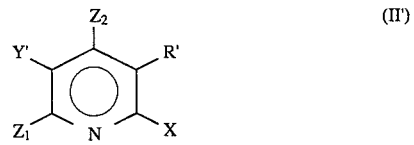

wherein one of R' and Y' is halogen and the other is nitro, cyano, or trifluoromethyl; and X, $Z_1$ and $Z_2$ are as defined above, wherein the pyridine of the formula (I') is reacted with a halogenating agent to form a halogenopyridine of the formula (III'):

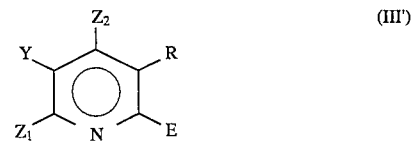

wherein E is —N(A)—Hal, wherein A is hydrogen; and Hal is halogen; and $Z_1$, $Z_2$, R and Y are as defined above, and said halogenopyridine of the formula (III') is subjected to a rearrangement reaction in the presence of a proton donor to form the 3-halogenopyridine of the formula (II').

2. The method according to claim 1, wherein the halogenating agent is N-halogenosuccinimide, N-halogenophthalimide, tert-butyl hypohalide, chlorine, bromine, trihalogenoisocyanuric acid or a salt thereof, dihalogenoisocyancuric acid or a salt thereof, or a halogeno-3-halogenopyridine of the formula (IV):

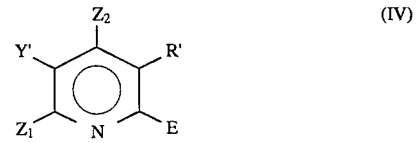

wherein R', Y', E, Z, and $Z_2$ are as defined above, and the proton donor is a carboxylic acid, succinimide, phthalamide or isocyanuric acid.

3. A method for producing a 3-halogenopyridine, which comprises subjecting a halogenopyridine of the formula (III'):

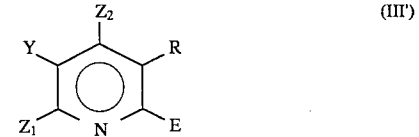

wherein E is —N(A)—Hal, wherein A is hydrogen; and Hal is halogen; each of $Z_1$ and $Z_2$ is hydrogen or halogen; and one of R and Y is hydrogen and the other is nitro, cyano or trifluoromethyl, to a rearrangement reaction in the presence of a proton donor to obtain a 3-halogenopyridine of the formula (II'):

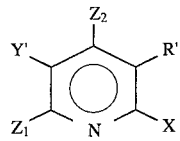
(II')

wherein one of R' and Y' is halogen and the other is nitro, cyano, or trifluoromethyl, X is amino; and $Z_1$ and $Z_2$ are as defined above.

4. A halogenopyridine compound of the formula (V):

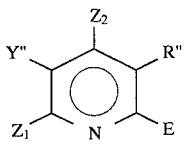
(V)

wherein E is —N(A)—Hal, wherein A is hydrogen; and Hal is halogen; each of $Z_1$ and $Z_2$ is hydrogen or halogen; one of R" and Y" is hydrogen or halogen and the other is nitro, cyano or trifluoromethyl.

5. The method according to claim 1, wherein a halogenating agent is the halogeno-3-halogenopyridine of the formula (IV), chlorine or bromine; and the proton donor is at least one carboxylic acid selected from the group consisting of formic acid, acetic acid and propionic acid.

6. The method according to claim 1, wherein the halogenation reaction is conducted at a temperature of from −20° C. to the refluxing temperature of the solvent, and the rearrangement reaction is conducted at a temperature of from 0° C. to the refluxing temperature of the solvent.

7. The method according to claim 1, wherein the 3-halogenopyridine of the formula (II') is halogenated to form a halogeno-3-halogenopyridine, and the pyridine of the formula (I') is halogenated with said halogeno-3-halogenopyridine to form the halogenopyridine of the formula (III'), which is then subjected to the rearrangement reaction to form the 3-halogenopyridine of the formula (II').

8. The method according to claim 1, wherein 2-amino-5-trifluoromethylpyridine, 2-amino-5-nitropyridine or 2-amino-5-cyanopyridine is reacted with chlorine to form 2-chloroamino-5-trifluoromethylpyridine, 2-chloroamino-5-nitropyridine or 2-chloroamino-5-cyanopyridine, respectively, which is then subjected to a rearrangement reaction in the presence of at least one carboxylic acid selected from the group consisting of formic acid, acetic acid and propionic acid, to obtain 2-amino-3-chloro-5-trifluoromethylpyridine, 2-amino-3-chloro-5-nitropyridine or 2-amino-3-chloro-5-cyanopyridine.

9. The method according to claim 1, wherein 2-amino-5-trifluoromethylpyridine is reacted with chlorine to form 2-chloroamino-5-trifluoromethylpyridine, which is then subjected to a rearrangement reaction in the presence of at least one carboxylic acid selected from the group consisting of formic acid, acetic acid and propionic acid to obtain 2-amino-3-chloro-5-trifluoromethylpyridine.

10. The method according to claim 1, wherein the chlorination reaction is conducted at a temperature of from −20° C. to +20° C., and the rearrangement reaction is conducted at a temperature of from 0° C. to the refluxing temperature of the solvent.

* * * * *